United States Patent
Bourne et al.

(10) Patent No.: US 6,343,512 B1
(45) Date of Patent: Feb. 5, 2002

(54) ULTRASOUND PROBE INCLUDING A HYDROPHILIC COUPLANT

(75) Inventors: Simon Bourne, Milton Keynes; Donald James Highgate, Surrey; Wayne Woodhead, Essex; Marcus Newborough, Bedfordshire, all of (GB)

(73) Assignee: Cranfield University, Bedfordshire (GB)

( * ) Notice: Subject to any disclaimer, the term of this patent is extended or adjusted under 35 U.S.C. 154(b) by 0 days.

(21) Appl. No.: 09/396,435

(22) Filed: Sep. 15, 1999

(30) Foreign Application Priority Data

Sep. 15, 1998 (GB) ............................................. 9820119

(51) Int. Cl.[7] ............................ G01N 29/04; A61B 8/14
(52) U.S. Cl. ........................................ 73/644; 600/459
(58) Field of Search ........................... 73/644, 620, 622, 73/627, 629, 632, 639; 600/437, 459

(56) References Cited

U.S. PATENT DOCUMENTS

| | | | | |
|---|---|---|---|---|
| 3,826,127 A | * | 7/1974 | Molina | 73/644 |
| 3,921,442 A | | 11/1975 | Soloway | 73/644 |
| 4,365,516 A | * | 12/1982 | Molina | 73/644 |
| 4,459,854 A | * | 7/1984 | Richardson et al. | 73/644 |
| 4,703,656 A | * | 11/1987 | Bhardwaj | 73/644 |
| 4,795,935 A | * | 1/1989 | Fujie et al. | 73/644 |
| 4,905,700 A | * | 3/1990 | Wokalek et al. | 73/644 |
| 5,477,729 A | * | 12/1995 | Cavalloni | 73/644 |
| 6,030,676 A | * | 2/2000 | Cottin et al. | 428/64.1 |
| 6,039,694 A | * | 3/2000 | Larson et al. | 73/644 |

* cited by examiner

*Primary Examiner*—Helen Kwok
(74) *Attorney, Agent, or Firm*—Oliff & Berridge, PLC

(57) ABSTRACT

An ultrasound probe includes a cross-linked hydrophilic material as an integral couplant, wherein the hydrophilic material is capable of transmitting a frequency in the range of 5 to 20 MHz, and wherein the attenuation of the transmission is less than 1.5 dB.mm$^{-1}$ at 5 MHz. For example, the invention provides a wheel-type probe, where the hydrophilic material 19 forms the tire.

31 Claims, 1 Drawing Sheet

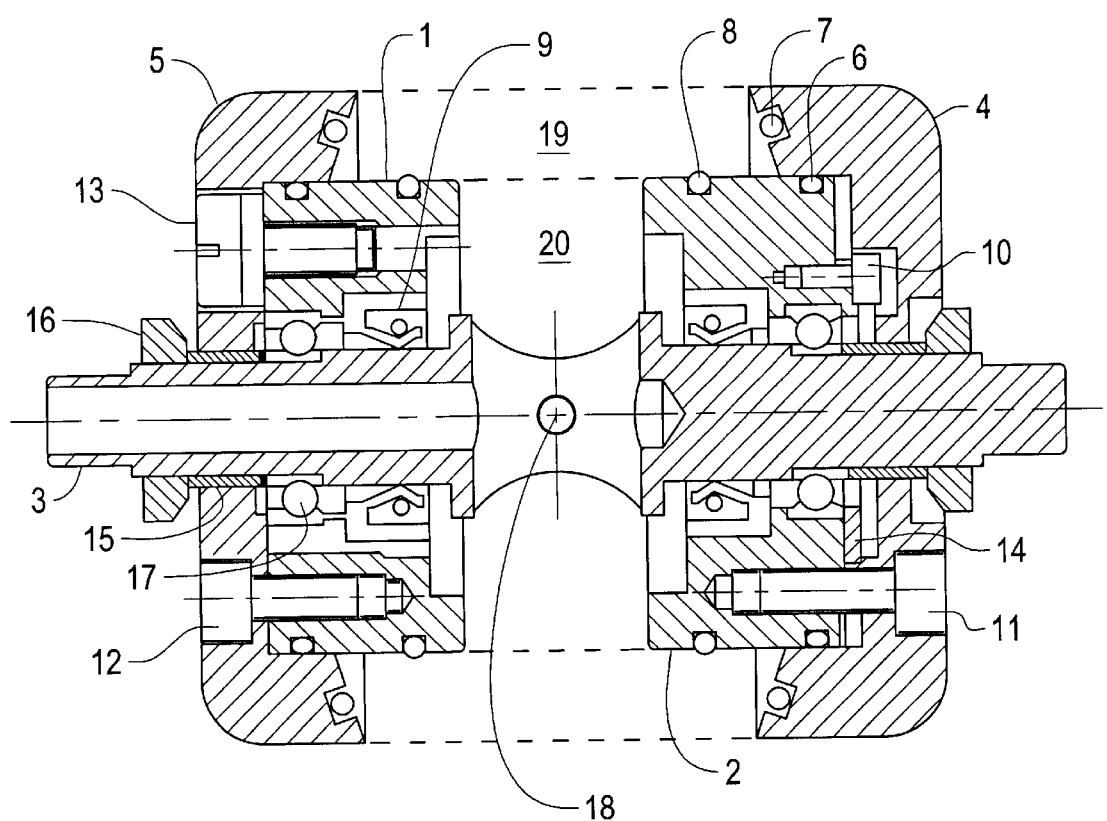

ULTRASOUND PROBE INCLUDING A HYDROPHILIC COUPLANT

FIELD OF THE INVENTION

This invention relates to ultrasound probes including a hydrophilic couplant.

BACKGROUND OF THE INVENTION

The testing and examination of complex structures, without damaging them, is now of immense importance in a wide range of industrial and medical situations. The use of ultrasound is perhaps the most ubiquitous such methodology. It is now used both to detect and characterise static defects or anomalies in metal or fibre composite structures, and to image biological systems in real time. A large range of techniques, from simple manual scanning to computer-controlled multi-axis tomography systems, are in use or under development.

The testing process involves generating an ultrasound beam from a source of ultrasound (normally a piezoelectric crystal) and introducing the sonic energy into the specimen to be examined. A detector is then arranged to receive the energy that is reflected, transmitted or scattered, depending upon the operating system and the objectives of the examination. The resolution of the process depends in part upon the frequency of the ultrasound used; high frequencies are needed to resolve small defects, and thus the frequency range now used in ultrasonic examination is typically 1–50 MHz.

In all cases, there is a need to introduce the interrogating beam into the specimen and remove the resulting sonic signal after passage through the specimen through the surface of the specimen. In most cases, it is convenient for the specimen to be surrounded by air, but the interface, i.e. sample→air→transducer, represents a discontinuity at which sonic energy is lost by mismatch, scattering or reflection, thus seriously reducing the effectiveness of the test process. In addition, the effect of a given air gap varies with the frequency of the applied signal, becoming more significant as the frequency increases.

To overcome the mismatch at the air interface between the transducers (generation and detection) and the specimen, liquid and dry couplants have been applied. Thus, in one case, the air gap is eliminated by filling it with a liquid, of which the most common is water. For automatic scanning, the jet probe has been developed. In this device, a water jet is directed from the generating transducer onto the target, and the ultrasound passes through the continuous water layer to the specimen. This works well, provided that the specimen is resistant to water or can be completely dried after examination. This method is the most widely used technique in the aerospace industry, for producing through C-scans of large components; its limitations include: the need to maintain laminar flow in the water jet, which limits the geometries that can be examined; the difficulty in properly removing all the water from a complex structure, which is especially important in those structures that are susceptible to corrosion, the requirement for pumping equipment; and the difficulty in avoiding air bubbles that may influence results undesirably.

A number of high viscosity aqueous gels have been developed to allow water to be applied in a form which will reduce run-off or pooling, but such materials do not accommodate large surface deformation nor do they prevent the water from drying up quickly and disturbing the examination. They also require careful cleaning of the specimen, if their removal is necessary. They exhibit high attenuation and/or can be used only at low transmission frequencies.

As an alternative to liquid couplants, a range of soft elastic (polymeric) materials has been developed, conventionally based upon natural or artificial rubbers which are applied as "pads" to make contact between the transducer and the specimen, or in the form of tires when applied to a wheel probe. This class of device is pressed onto the surface of the specimen and tracked over the surface to build up a picture of the subsurface over a significant area; one application is the detection of cracks in railway track, when the intention is to examine some miles of track at any one time. However, considerable pressure is often required to ensure a good contact, and this is not always possible. Further, existing materials do not have the necessary ultrasound properties to make a good match between the transducer and the range of specimen materials available. They exhibit high attenuation and/or can be used only at low transmission frequencies.

Desirably, a couplant material should be safe and readily manufactured into a range of coupling systems. In addition, it should satisfy the following requirements:

(i) show low attenuation to ultrasound;

(ii) be transparent to a wide range of acoustic frequencies;

(iii) posses an acoustic impedance similar to that of common specimen materials, so as to reduce energy reflection or scattering at the interface (and ideally offer the possibility of controlling the impedance to match other systems); and (iv) possess a structure which allows the elastic properties to be varied widely (to make it possible to couple to surfaces of differing mechanical properties and shapes).

Cross-linked hydrophilic materials are characterized by the ability to take in large amounts of water, or other polar liquids, and reach a state of stable hydration without suffering solution or long-term degradation. Such materials are now readily available having equilibrium water contents in the range 10 to 98% by wet weight (i.e. materials which absorb up to 15 times their dry weight). Until recently, they found application only in ophthalmic optics. However, their mechanical stability, and the ability to control their hydraulic properties (water uptake and permeability), and their gas permeability, when hydrated, have led to a number of other applications in the fields of bio-implants, wound care and drug release where the safety of the materials has been established over a long period of time.

U.S. Pat. No. 3,921,442 discloses an ultrasound probe including a hydrophilic polymer couplant. The only polymer that is disclosed is polyHEMA, i.e. a homopolymer of 2-hydroxyethyl methacrylate. This has a maximum water content of about 38%, and insufficient strength for any dynamic application. PolyHEMA is not capable of transmitting a frequency above 5 MHz, without high attenuation of the transmitted signal. It is noteworthy that there is no disclosure of any specific device or use of the couplant, in U.S. Pat. No. 3,921,442.

It is clear that no single material or combination of materials now in use fulfills the requirements for ultrasound couplants, given above. In particular, their acoustic impedance is generally low.

SUMMARY OF THE INVENTION

The present invention is based on the discovery that, although U.S. Pat. No. 3,921,442 discloses a system unsuitable for commercial use, certain cross-linked hydrophilic copolymers are suitable and effective for use as ultrasonic couplants, notably in fault detection systems. According to the present invention, an ultrasound probe includes, in addition to conventional components such as a source of ultrasound or means of transmitting ultrasound from a remote source, a cross-linked hydrophilic material as an integral couplant; the hydrophilic material is capable of transmitting a frequency in the range of 5 to 20 MHz, and exhibits attenuation of the transmission of less than 1.5, and preferably less than 1, dB.mm$^{-1}$ at 5 MHz. It is not essential that the material is capable of transmitting at all frequencies in the given range, although that may be preferred; it may also be capable of transmission at frequencies above 20 MHz. Nor is it essential that the probe is used to transmit frequencies in the given range.

A probe according to the present invention can be simple and portable. Its use avoids damage to structures caused by the action of free water. There is no requirement for water pumping equipment or water tanks. The test piece can be of any size. It may also be non-regular in shape or have a rough surface.

The hydrophilic material can be supplied as in integral part of the probe, or independently, and in a range of acoustic impedances allowing close matching to that of the test structure. Further, hydrophilic materials can combine the advantages of dry and liquid couplants, without their disadvantages. Thus, for example, by contrast to gels, a hydrophilic material can be combined with an ultrasound probe to provide an integral device, e.g. by using the shrink-fitting properties of hydrophilic materials. Further, unlike gels, the cross-linked nature of such hydrophilic materials prevents them from flowing. Therefore, they are spatially defined, and as such, combinations of hydrophilic materials can be used, e.g. with the aim of focusing the ultrasound waves. The invention allows the use of polymers whose properties can be varied controllably within a given couplant device.

BRIEF DESCRIPTION OF THE DRAWINGS

The accompanying drawing is a cross-sectional view of a probe device that embodies the present invention.

DESCRIPTION OF THE INVENTION

The acoustic properties of hydrophilic polymers with respect to ultrasound transmission, and the properties/conditions governing the transmission of ultrasound across hydrophilic polymer-other material interfaces, are good. In addition, trials have shown that a surface contact pressure as low as 0.2 kg.cm$^{-2}$ (in the case of a 60% hydrated hydrophilic polymer) are required to achieve optimal coupling efficiency to a smooth steel block.

The present invention utilises the great potential for hydrophilic polymers in terms of frequency and amplitude of signal over materials currently used in dry coupling applications. Samples have demonstrated an ability to transmit a wide range of frequencies, e.g. over 12 MHz. This is significantly higher than for natural rubber and also a current wheel-probe rubber, offering previously unattainable potential for high-resolution ultrasonic inspection/evaluation.

In use, the hydrophilic material should be hydrated. For the purposes of this specification, the term "hydrated" refers to wetting with water or any other suitable polar liquid. If desired, the hydrophilic material may be supplied with low or no hydration, and can be hydrated at the point of use. In certain circumstances, it may be desirable to provide means for hydration of the material. Hydration means may also be useful to maintain the degree of hydration of the material, over an extended period of use. If the material is supplied hydrated, it may be desirable, in order to prevent loss of liquid, to seal it, e.g. by using a cap on the probe.

The hydrophilic material that is used in the invention can be chosen according to its desired properties, or with respect to the intended specimen for investigation, so that the materials are well matched. For use in a static application, or more generally for short duration use or if the probe is intended to be disposable, the hydrophilic material may have relatively low tear strength, typically of less than 10 kg/cm$^2$, e.g. 2–3 kg/cm$^2$. Particularly for use in dynamic applications, the hydrophilic material preferably has a relatively high tear strength, typically of at least 10–15 kg/cm$^2$, e.g. up to 40 kg/cm$^2$. The latter will be particularly appropriate for use with a self-hydrating wheel-type transducer.

By way of example, the hydrophilic material may be a (co)polymer of a (meth)acrylate, optionally with a hydrophilic copolymerisable monomer. Certain copolymers are preferred, especially when the maximum water uptake of the material is dependent on the relative amounts of the respective monomers. Examples of suitable hydrophilic materials having relatively low tear strength are HEMA:VP or MMA:VP (VP is vinyl pyrrolidone, and MMA is methyl methacrylate), Examples of suitable hydrophilic materials having relatively high tear strength are AN:VP, HEMA:MMA or polyamide:VP (AN is acrylonitrile).

During the absorption of liquid, hydrophilic material normally swells isotropically and changes from a hard rigid structure, becoming soft and elastic when fully hydrated. This dramatic transformation, which also allows the material to be used in medicine and engineering means that a device can be accurately machined and polished when the material is dry, and subsequently hydrated to become soft, conforming and bio-compatible. The linear expansion ratio ($X_{wet}/X_{dry}$), e.g. between 1.1 and 3.5, may be accurately controlled.

Cross-linked hydrophilic copolymers are not generally thermoplastic. Consequently, they show great stability and are normally flame-retardant, charring at high temperatures in air rather than burning. Their processing may be complex and relatively costly; composite systems involving "dispersed phase" systems of hydrophilic materials may be preferred. These systems typically involve a dispersion of hydrophilic particles in an elastic hydrophilic or thermoplastic matrix. By controlling the particle size and volume concentration of the hydrophilic particles, the overall expansion ratio and permeability of the final product may be controlled. In this way, complex properties can be engineered into the finished product while retaining the essential polar liquid and gas transmission abilities of the hydrophilic materials.

Hydrophilic copolymers can have a wide range of liquid uptake characteristics, for example, from 40% or 50% by wet weight water to 95% by wet weight water. This figure may represent hydration at any level, typically substantially complete hydration. The preferred characteristic may be the amount or liquid in the material.

Such materials can be prepared and applied as a couplant in several physical forms. Examples are:
  (a) as a continuous solid polymer, when its liquid content can be varied to provide the optimum measure of the test body;
  (b) as a hydrated powder, which can be shaped to choice and in which the particle size and size distribution can be varied, to control the physical properties of the resulting 'mass';

(c) as a hydrated powder containing additional non-hydrophilic materials, to control the acoustic properties of the overall structure; and (d) as a combination of hydrophilic materials, combined to produce a solid couplant capable of altering the acoustic impedance and/or the mechanical properties of the coupling agent.

Option (d) is one example of a preferred embodiment of the invention, in which the hydrophilic material is anisotropic. This may be achieved by having an additional hydrophilic or a non-hydrophilic material dispersed in the couplant, whereby the acoustic impedance and/or the mechanical property of the couplant is controlled. Further, desirable anisotropy may be the consequence of using a non-planar configuration for the couplant, as in the case of a wheel-type probe, As indicated above, the (re)hydrating liquid is a polar liquid. As such, water, alcohol and various non-freezing solutions can be used, as may be appropriate, and with a number of different advantages.

Tests have established that hydrophilic materials possess the capability to operate as improved couplant materials. It will be appreciated that the nature or type of material may be different, to provide optimal performance for different applications, i.e. for use against specimen materials of differing ultrasonic and mechanical properties, and in different formats (in conjunction with static or wheel-type transducers). In an ideal couplant, its acoustic impedance should be matched to that of the specimen, and all existing couplants are low as compared with common metals.

In the form of a continuous solid polymer, the couplant can either be attached to the probe, for example, as the tire of a wheel-type transducer or affixed to the tip of a static probe, or it can be applied to the target structure independently of the probe.

A preferred embodiment of the present invention, i.e. a wheel-type transducer, is illustrated in FIG. 1. Any feature shown in and described with reference to the drawing may be more generally applicable to the breadth of the invention.

FIG. 1 shows bearing housings 1,2 mounted on a shaft 3, within an adjustable tire support 4 and a fixed support 5. O-rings 6–8 are also shown, as are a lip seal 9, screws/nuts 10,11,12, a screw plug 13, a retaining plate 14, a spacer 15, a bearing lock nut 16, and a deep-groove ball bearing 17.

The central, convex part of the shaft includes a central aperture 18, within which may be housed an ultrasound source such as a piezoelectric crystal (not shown). A hydrophilic material 19 (outlined by dotted lines), in tubular or tire form, is fitted around the bearing housings. The tube defines a contained space 20. If necessary or desired, water may be retained in this space. This serves to (re)hydrate the hydrophilic material.

The following Examples illustrate the invention.

EXAMPLES

Four commercially-available hydrophilic polymers were tested as couplants. These are defined below as the 38%, 50%, 60% and 75% materials, respectively, indicating their water content at full hydration, with respect to the hydrated weight. The first or these materials was polyHEMA: the other three were used to illustrate the invention, and are copolymers of polymethyl methacrylate and vinylpyrrolidone. These materials demonstrated a wide range of different mechanical properties (elasticity and tear strength) and would therefore be expected to be suited to different applications.

These four materials were tested in comparison with rubber and water, as ultrasound couplants. Results are shown in the following Table.

| Sample | Density ($Kg.m^{-3}$) | Ultrasonic Velocity ($m.sec^{-1}$) | Acoustic Impedance ($MN.s.m^{-3}$) | Attenuation ($dB.mm^{-1}$ at 5 MHz) |
|---|---|---|---|---|
| 38% | 1322 | 1662 | 2.20 | 1.75 |
| 50% | 1123 | 1691 | 1.90 | 0.84 |
| 60% | 1096 | 1672 | 1.83 | 0.60 |
| 75% | 1085 | 1590 | 1.72 | 0.41 |
| Natural Rubber | 1050 | 1455 | 1.53 | — |
| Distilled Water | 998 | 1497 | 1.49 | — |
| Aluminium | 2700 | 6350 | 17.14 | — |

As can be seen, the acoustic impedance measured, for the continuous unloaded hydrophilic materials was usefully higher than for any existing couplant material. The method of manufacture of the hydrophilic materials allows for the inclusion of loadings of material which may permit the modification of this property. Attenuation (which was too high for measurement in the case of rubber) is surprisingly low for the hydrated MMA:VP copolymers.

Samples of hydrophilic material of differing thickness were compared with aluminium (which is accepted as being effectively transparent to ultrasound at commonly used frequencies). A piezoelectric crystal was used whose greatest amplitude of transmission was at 10 MHz. The results for 38%, 60% and 75% materials show that the materials were excellent transmitters of ultrasonic energy up to the maximum frequency tested, i.e. 20 MHz, although this depended (as might be expected) upon water content. All the polymers tested transmit higher frequencies than natural rubber and a commonly used dry contact rubber. The upper frequency limit has yet to be determined. The amplitude of the higher frequencies increased with water content and decreased with polymer thickness.

It may be noted that the ultrasonic properties of the AN-VP hydrophilic polymers do not change excessively as a result of pressure. Indeed, in one case, a backwall echo obtained, using the 60% polymer acting as a dry couplant on steel, demonstrated virtually no change at all in frequency and amplitude over the range of pressures employed within this study. The 38% (HEMA) sample showed a more noticeable change in ultrasonic properties with varying pressure, suggesting that mechanical pressure affects its ultrasonic performance.

The higher the water content of the polymers tested, the greater the rate of dehydration observed during life testing. One of the greatest rates of dehydration measured was that of the 60% polymer, at 32.28 weight % per hour. Even at this rate, the actual amount of water lost over three hours is in fact less than 1 g. This indicates that only small quantities of water may be required to maintain hydration during operation.

What is claimed is:

1. An ultrasound probe which includes a cross-linked hydrophilic material as an integral couplant, wherein the hydrophilic material is capable of transmitting a frequency in the range of 5 to 20 MHz, and wherein an attenuation of the transmission is less than 1.5 $db.mm^{-1}$ at 5 MHz, said hydrophilic material is a copolymer of vinylpyrrolidone and a (meth)acrylate, wherein a maximum water uptake of the material is dependent on the relative amounts of respective hydrophilic monomers, and wherein the probe is in the form of a wheel and said hydrophilic material forms the wheel.

2. A probe according to claim 1, wherein said hydrophilic material has a maximum water uptake dependent on the relative amounts of an respective hydrophilic monomers.

3. A probe according to claim 2, wherein said hydrophilic material is optionally with a copolymerisable hydrophilic monomer.

4. A probe according to claim 2, wherein said hydrophilic material is HEMA:VP or MMA:VP.

5. A probe according to claim 2, wherein said hydrophilic material is AN:VP, HEMA:MMA or polyamide:VP.

6. A probe according to claim 1, wherein said hydrophilic material contains at least 40% w/w of a polar liquid.

7. A probe according to claim 6, wherein said hydrophilic material contains at least 50% w/w of a polar liquid.

8. A probe according to claim 1, wherein said hydrophilic material is at least substantially fully hydrated with a polar liquid.

9. A probe according to claim 8, wherein said polar liquid is water.

10. A probe according to claim 1, wherein said hydrophilic material is anisotropic.

11. A probe according to claim 10, wherein said hydrophilic material has, dispersed therein, an additional hydrophilic or a non-hydrophilic material, whereby an acoustic impedance and/or a mechanical property of the couplant is controlled.

12. A probe according to claim 10, which comprises two or more different hydrophilic materials, whereby an ultrasound signal is focused.

13. A probe according to claim 1, wherein said hydrophilic material exhibits a tear strength of at least 15 kg/cm$^2$.

14. A probe according to claim 1, wherein said attenuation is less than 1 dB.mm$^{-1}$ at 5 MHz.

15. A probe according to claim 1, which additionally comprises means for hydration of the couplant.

16. An ultrasound probe comprising:
a cross-linked hydrophilic material as an integral couplant, wherein the hydrophilic material is capable of transmitting a frequency in the range of 5 to 20 MHz, and wherein an attenuation of the transmission is less than 1.5 dB.mm$^{-1}$ at 5 MHz; and
said probe is in the form of a wheel and said hydrophilic material forms the wheel.

17. A probe according to claim 16, wherein said hydrophilic material has a maximum water uptake dependent on the relative amounts of a respective hydrophilic monomers.

18. A probe according to claim 17, wherein said hydrophilic material is optionally with a copolymerisable hydrophilic monomer.

19. A probe according to claim 17, wherein said hydroliphilic material is HEMA:VP or MMA:VP.

20. A probe according to claim 17, wherein said hydrophilic material is AN:VP, HEMA:MMA or polyamide:VP.

21. A probe according to claim 16, wherein said hydrophilic material contains at least 40% w/w of a polar liquid.

22. A probe according to claim 21, wherein said hydrophilic material contains at least 50% w/w of a polar liquid.

23. A probe according to claim 16, wherein said hydrophilic material is at least substantially fully hydrated with a polar liquid.

24. A probe according to claim 23, wherein said polar liquid is water.

25. A probe according to claim 16, wherein said hydrophilic material is anisotropic.

26. A probe according to claim 25, wherein said hydrophilic material has, dispersed therein, an additional hydrophilic or a non-hydrophilic material, whereby an acoustic impedance and/or a mechanical property of the couplant is controlled.

27. A probe according to claim 25, which comprises two or more different hydrophilic materials, whereby an ultrasound signal is focused.

28. A probe according to claim 16, wherein said hydrophilic material exhibits a tear strength of at least 15 kg/cm$^2$.

29. A probe according to claim 16, wherein said attenuation is less than 1 dB.mm$^{-1}$ at 5 MHz.

30. A probe according to claim 16, which additionally comprises means for hydration of the couplant.

31. An ultrasound probe comprising:
a cross-linked hydrophilic material as an integral couplant, wherein the hydrophilic material is capable of transmitting a frequency in the range of 5 to 20 MHz, and wherein an attenuation of the transmission is less than 1.5 db.mm$^{-1}$ at 5 MHz;
said probe is in the form of a wheel and said hydrophilic material forms the wheel; and
said hydrophilic material exhibits a tear strength of at least 15 kg/cm$^2$.

* * * * *